(12) United States Patent
McDonald

(10) Patent No.: US 8,262,727 B2
(45) Date of Patent: *Sep. 11, 2012

(54) INTRAOCULAR MULTIFOCAL LENS

(76) Inventor: Marguerite B. McDonald, New Orleans, LA (US)

( * ) Notice: Subject to any disclaimer, the term of this patent is extended or adjusted under 35 U.S.C. 154(b) by 1234 days.

This patent is subject to a terminal disclaimer.

(21) Appl. No.: 11/464,005

(22) Filed: Aug. 11, 2006

(65) Prior Publication Data

US 2006/0293747 A1 Dec. 28, 2006

Related U.S. Application Data

(63) Continuation of application No. 10/706,630, filed on Nov. 12, 2003, now Pat. No. 7,144,423.

(51) Int. Cl.
*A61F 2/16* (2006.01)

(52) U.S. Cl. ............... 623/6.13; 623/6.23; 623/6.27

(58) Field of Classification Search .......... 623/6.23, 623/6.24, 6.27, 6.29, 6.4, 6.13

See application file for complete search history.

(56) References Cited

U.S. PATENT DOCUMENTS

| | | | | |
|---|---|---|---|---|
| 3,809,092 | A * | 5/1974 | Abraham | 606/107 |
| 4,074,368 | A * | 2/1978 | Levy et al. | 623/6.13 |
| 4,102,567 | A * | 7/1978 | Cuffe et al. | 351/160 R |
| 4,174,156 | A * | 11/1979 | Glorieux | 351/168 |
| 4,373,218 | A * | 2/1983 | Schachar | 623/6.13 |
| 4,512,040 | A * | 4/1985 | McClure | 623/6.13 |
| 4,769,033 | A * | 9/1988 | Nordan | 623/6.24 |
| 4,778,462 | A * | 10/1988 | Grendahl | 623/6.27 |
| 4,898,461 | A * | 2/1990 | Portney | 351/169 |
| 4,932,966 | A * | 6/1990 | Christie et al. | 623/6.13 |
| 5,117,306 | A * | 5/1992 | Cohen | 359/565 |
| 5,522,891 | A * | 6/1996 | Klaas | 623/6.37 |
| 5,562,731 | A * | 10/1996 | Cumming | 606/107 |
| 5,728,156 | A * | 3/1998 | Gupta et al. | 623/6.26 |
| 6,533,813 | B1 * | 3/2003 | Lin et al. | 623/6.37 |
| 6,871,953 | B1 * | 3/2005 | Mandell et al. | 351/161 |
| 6,921,416 | B2 * | 7/2005 | Khoury | 623/6.37 |
| 6,986,763 | B2 * | 1/2006 | Holmen | 604/521 |
| 7,144,423 | B2 * | 12/2006 | McDonald | 623/6.27 |
| 2006/0212116 | A1 * | 9/2006 | Woods | 623/6.13 |

* cited by examiner

*Primary Examiner* — Paul Prebilic
(74) *Attorney, Agent, or Firm* — Wayne Edward Ramage; Baker Douelson

(57) ABSTRACT

In accordance with the present invention, a multifocal intraocular lens provides greater or lesser refraction in relation to the position of the head and eyes of a user. A multifocal intraocular lens body for insertion into a fluid-filled enucleated natural lens capsule of an eye is provided wherein the lens body encompasses the optical axis of the eye and provides different greater or lesser refraction depending upon the position of the eye.

13 Claims, 7 Drawing Sheets

INTRAOCULAR MULTIFOCAL LENS

This application is a continuation of U.S. patent application Ser. No. 10/706,630, filed Nov. 12, 2003, by Marguerite B. McDonald, now issued as U.S. Pat. No. 7,144,423, and is entitled to that filing date for priority. The specification and drawings of U.S. patent application Ser. No. 10/706,630 and U.S. Pat. No. 7,144,423 are incorporated herein in their entireties by reference.

TECHNICAL FIELD OF THE INVENTION

This invention relates to intraocular lenses (IOLs), specifically, to IOLs that may have a plurality of refractive indices.

BACKGROUND OF THE INVENTION

The human eye includes an anterior chamber between the cornea and iris, a posterior chamber, defined by a capsular bag, containing a crystalline lens enclosed by a clear capsule, a vitreous chamber behind the lens containing the vitreous humor, and a retina at the rear of this chamber. The human eye has a natural accommodation ability. The constriction or contraction and relaxation of the ciliary muscle provides the eye with near and distant vision, respectively. This ciliary muscle action shapes the natural crystalline lens to the appropriate optical configuration for focusing light rays entering the eye on the retina. The removal of the natural lens leaves the eye with no means to focus at different distances and necessitates the use of bifocal lenses for near and far work.

Many different IOL designs have been developed over the years and proven successful in phakic and aphakic eyes. IOL implants have been used for years in aphakic eyes as replacements for diseased natural crystalline lenses that have been surgically removed from the eyes. IOLs for aphakic eyes are now implanted after cataract surgery in over 98% of the cases. Visual acuity deficiencies remaining after cataract surgery such as myopia (nearsightedness), hyperopia (farsightedness), and presbyopia (age-related farsightedness) are typically corrected with eyeglasses or contact lenses, though the accuracy of IOL power calculation has decreased the need for full-time postoperative spectacle use. The use of surgically implanted phakic IOLs as a permanent form of refractive correction has been gaining in popularity as well, though they are still considered investigational.

IOLs are generally of a fixed focal length. Fused bifocal and aspheric lenses have two or more optical focal planes that are engaged by changing the relationship of the light path or the observer to the lens. All such lenses require movement of either the lens (not possible with a standard IOL), light path, or observer to engage a different focal plane and can therefore be difficult to use. They also have an adverse effect on contrast sensitivity and can cause glare, halos, double vision (polyopia), and other optical aberration all of which compromises visual quality.

Accordingly, there is a need for a multifocal intraocular lens having a variable power of refraction that does not require deliberate engagement of different focal planes for near and far vision.

SUMMARY OF THE INVENTION

In accordance with the present invention, a multifocal intraocular lens provides greater or lesser refraction in relation to the position of the head and eyes of a user. A multifocal intraocular lens body for insertion into a fluid- or gel-filled enucleated natural lens capsule of an eye is provided wherein the lens body encompasses the optical axis of the eye and provides different greater or lesser refraction depending upon the position of the eye. In another embodiment, the lens body can be used with an artificial lens capsule implanted within an eye.

BRIEF DESCRIPTION OF THE DRAWINGS

For a more complete understanding of the present invention and for further advantages thereof, reference is now made to the following Description of the Preferred Embodiments taken in conjunction with the accompanying Drawings.

DETAILED DESCRIPTION OF THE INVENTION

Figure 1:
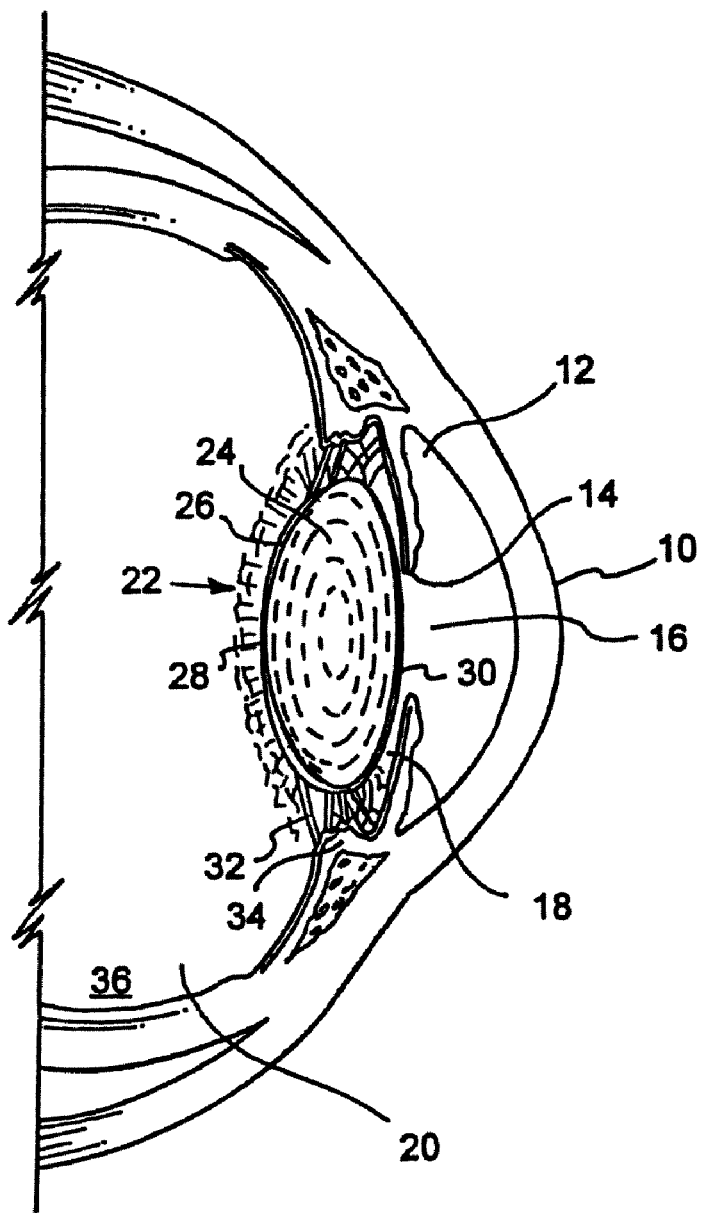
FIG. 1 is a sectional view of a human eye illustrating the basic components of the eye.

Turning now to these drawings and first to FIG. 1 for reference in the following description, the human eye comprises from front to rear an outer transparent cornea 10, an anterior chamber 12, an iris 14 containing a pupil 16, a posterior chamber 18, and a vitreous cavity 20. A natural lens 22 comprises a crystalline lens structure 24 contained within an optically clear bag called a lens capsule 26 having a posterior capsule 28 and an anterior capsule 30. The lens is peripherally joined by zonules 32 to the surrounding ciliary muscles 34. The vitreous cavity 20 contains vitreous 36.

The present invention is particularly useful in correcting the eye disorder known as a cataract which is characterized by progressive opacification of the natural lens 22 and resultant progressive attenuation of the light rays reaching the retina. Simply stated, this condition is corrected by removing the cataract, that is the cataractous (i.e. opaque) nucleus and cortex of the natural lens, and implanting an artificial intraocular lens in the eye. Cataract removal may be accomplished by intracapsular extraction (removal of the entire lens 22) or by extracapsular extraction (removal of the cataractous nucleus and cortex through the anterior side of the lens capsule 26) utilizing either nucleus expression through a relatively large opening in the eye or phacoemulsification through a relatively small opening in the eye.

The anterior capsule opening required for extracapsular extraction may be provided by (a) removing most of the anterior capsule 30 except small peripheral remnants of the anterior capsule, (b) tearing the anterior capsule to allow the human lens nucleus to be expressed, or (c) continuous tear circular capsulotomy, i.e. capsulorhexis. The essentially empty lens capsule 26 remaining after removal of the cataract is referred to as a capsular bag. Removal of the nucleus and cortex of the natural lens from the bag creates a space immediately behind the iris 14, between the latter and the posterior capsule 28 of the bag, which is approximately 10 mm in diameter and 5 mm front to back.

It is possible to implant an intraocular lens in any one or more of the eye chambers, i.e. anterior chamber 12, posterior chamber 18, capsular bag 26, or vitreous cavity 20. Intraocular implants according to the present invention may be placed in any one of these eye chambers or cavities. However, the invention is particularly concerned with an intraocular lens body for placement in a natural capsular bag having an anterior capsulotomy or in the anterior or posterior chambers, or in an artificial capsular bag and will be described primarily in these contexts.

Figure 2:
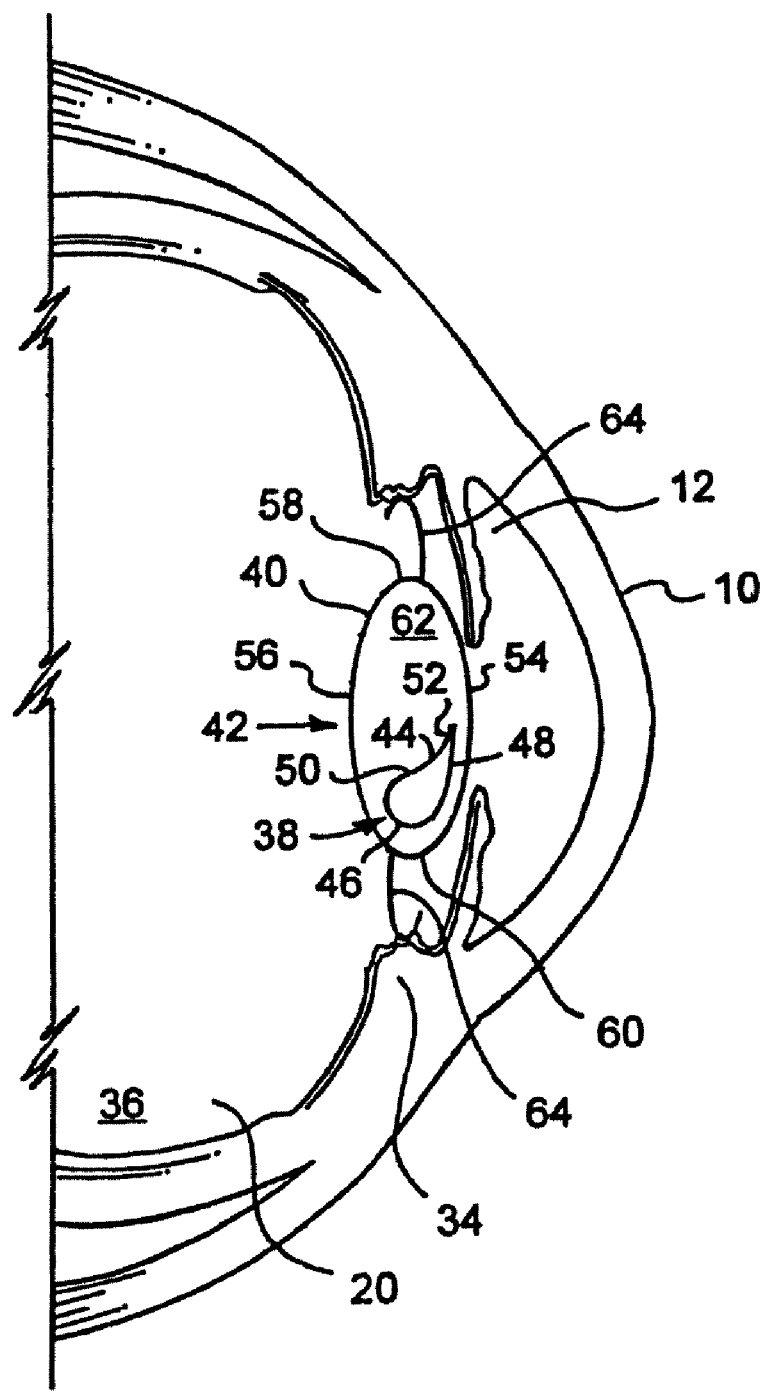
FIG. 2 is a sectional view of a human eye illustrating the present intraocular lens body inserted within the artificial capsule situated within an eye.
Figure 3:
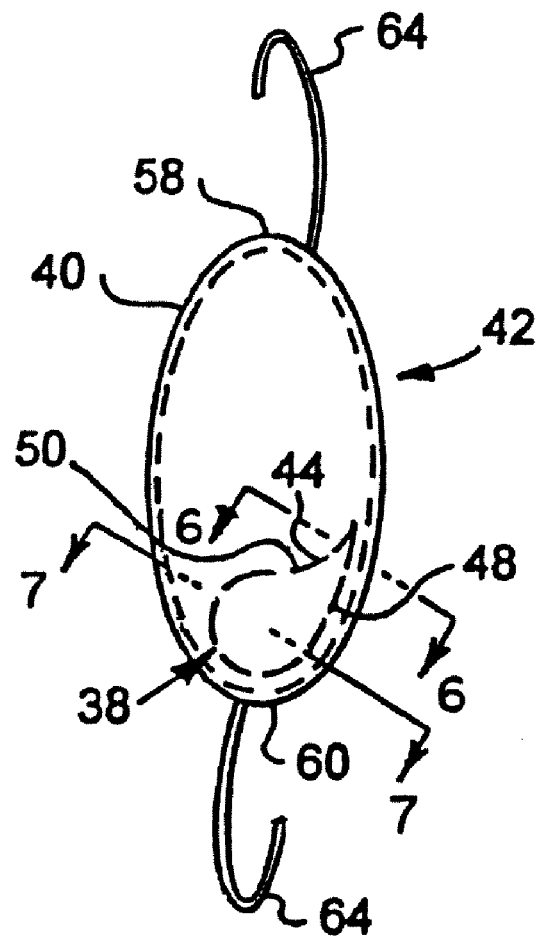
FIG. 3 is a side-elevated view of the present intraocular lens body and artificial capsule shown in FIG. 2.
Figure 4:
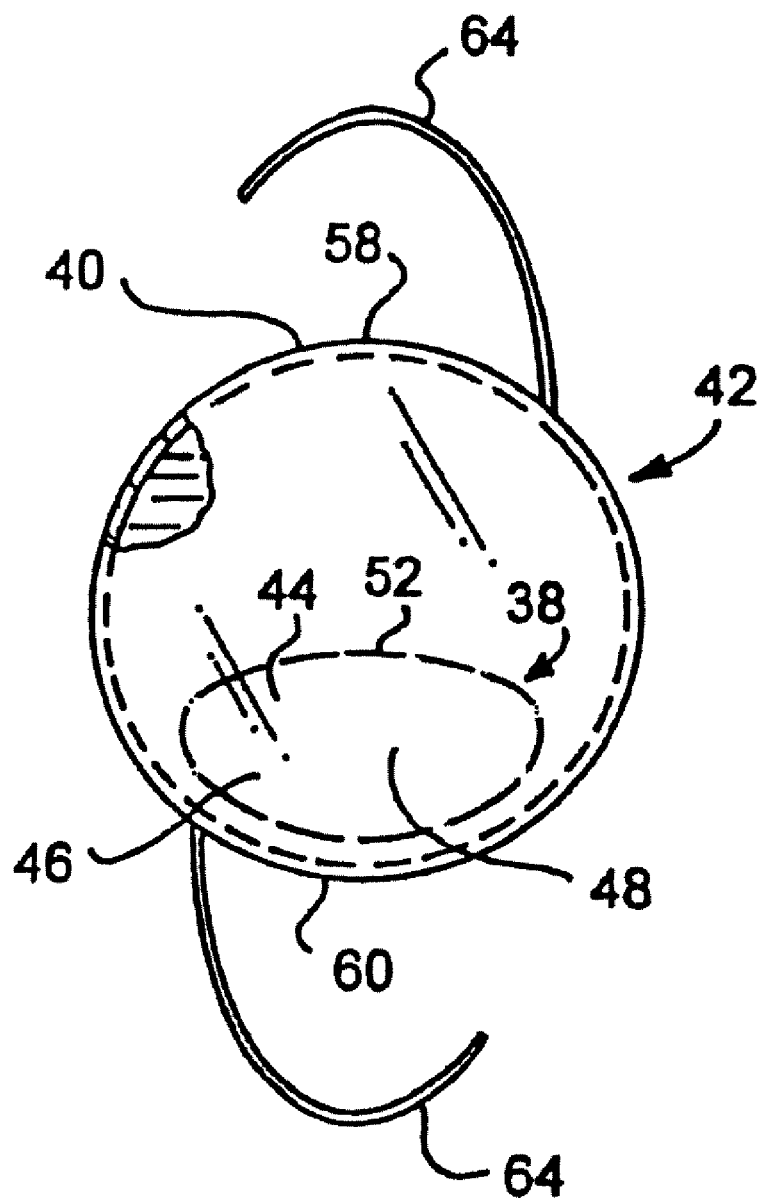
FIG. 4 is a plan view of the present intraocular lens body shown in FIG. 2.
Figure 6:
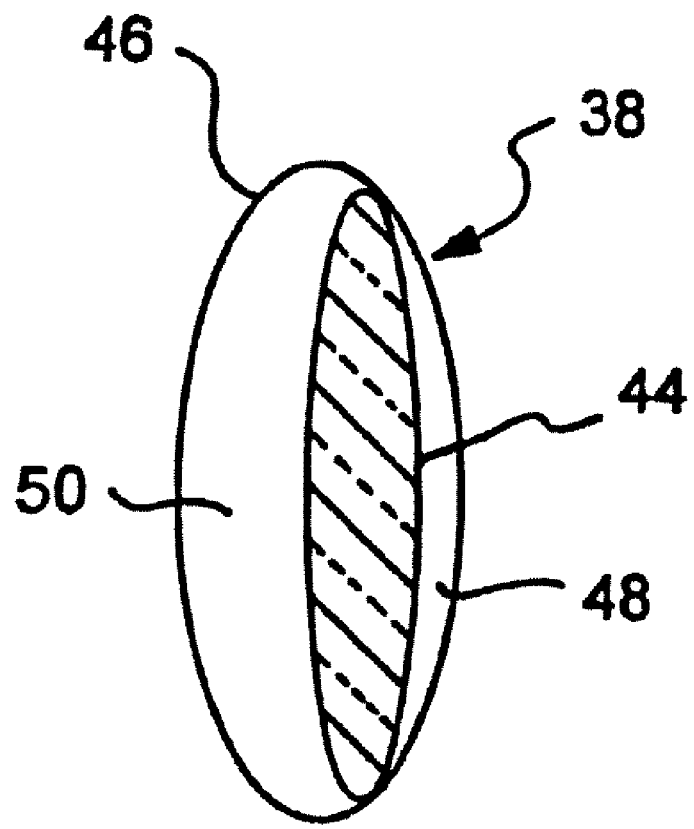
FIG. 6 is a sectional view of the present intraocular lens body through the line 6-6 of FIG. 3.
Figure 7:
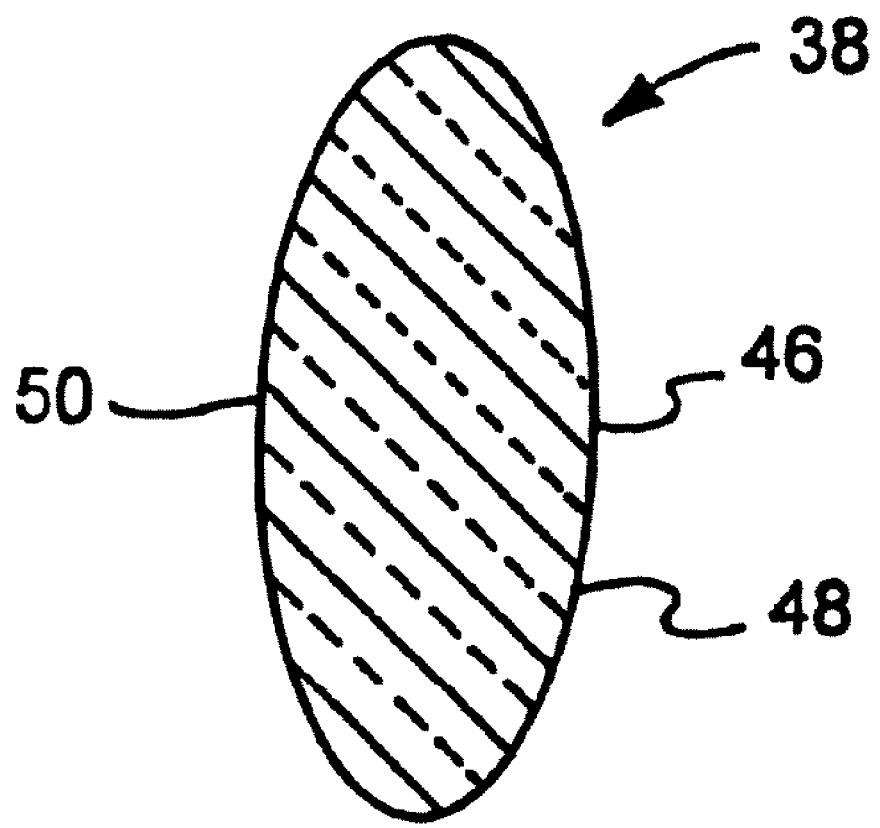
FIG. 7 is a sectional view of the present intraocular lens body through the line 7-7 of FIG. 3.

Referring now to FIGS. 2-4, in accordance with the present invention, there is illustrated multifocal intraocular lens body 38, positioned within an artificial capsular bag 40 to form a multifocal intraocular lens system 42, situated within a human eye from which the natural lens 22 has been removed (i.e. an aphakic eye). Multifocal intraocular lens body 38 has an upper portion 44, a lower portion 46, anterior surface 48, and a posterior surface 50. The following description of the lens body is as viewed from the medial-lateral axis. Anterior surface 48 and posterior surface 50 of lower portion 46 taper upwardly to form upper portion 44 to provide a tapering periphery 52. Anterior surface 48 and posterior surface 50 of upper portion 44 of lens body 38 each have at least one radius of curvature having its respective center positioned posteriorly the posterior surface 50 of lens body 38. An aspheric multifocal intraocular lens body is contemplated in one embodiment of the present lens body. At least one radius of curvature of posterior surface 50 of upper portion 44 of the lens body is preferably shorter than the radius of curvature of that along anterior surface 48 so as to form a comma-shaped lens body or any multifocal shape, preferably aspheric. Multiple radii of curvature are also contemplated as well as possibly a lens made of a material that increases in its index of refraction along the lens axes. As seen FIGS. 4, 6 and 7, the lens body is approximately elliptical when viewed anteriorly or posteriorly. The multifocal intraocular lens body may comprise any material suitable as a lens body and having a high index of refraction. Such material is preferably translucent and colorless, such as silicone, gel, or acrylic, and specifically may include polymethylmethacrylate (PMMA). However, such material may have a color for aesthetic or physiological purposes, e.g. to filter unwanted wavelengths such as those in the ultraviolet spectrum.

Multifocal intraocular lens body 38 is positioned within lens capsule 40. Lens capsule 40 has anterior surface 54, posterior surface 56, upper edge 58, and lower edge 60. Lens capsule 40 is approximately circular in shape and adapted to fit in the anterior or posterior chambers of an eye. Anterior surface 54 and posterior surface 56 completely encompass the optical axis formed by pupil 16. The distance between anterior surface 48 and posterior surface 56 of lens capsule 40 defines a thickness that corresponds to a first axis that extends generally perpendicularly between the surfaces. A second axis that is generally perpendicular to said first axis is also formed. The thickness of the lens capsule along the first axis is smaller than its width along its second axis. Lens capsule 40 can be made from a translucent and colorless pliable or substantially pliable material such as silicone or similar material, or other materials as would be known to one of skill in the art.

The multifocal intraocular lens body 38 is positioned within the lens capsule 40 so that lower portion 46 of lens body 38 lies adjacent to lower edge 60 of the lens capsule and anterior surface 48 of the lens body lies adjacent to anterior surface 54 of lens capsule 40. Tapering periphery 52 is the feature of lens body 38 that lies nearest to the approximate center of the lens capsule when the short axis of the lens capsule is parallel to the ground or as when the user is looking straight ahead. The approximate center of the lens capsule encompasses the optical axis of the eye. Multifocal intraocular lens body 38 provides only minimal additional refraction or no refraction consummate with the minimal or no additional refraction or required when looking at infinity, i.e. at the horizon. When anterior surface 54 of lens capsule 40 is tilted downwardly, lens body 38 moves towards upper edge 58 of the lens capsule and begins to "float" or slide more and more over the visual axis (i.e. the line of sight). After implantation, and when the user requires more focusing power, i.e. refraction, such as when reading, lens body 38 similarly slides upwards into the optical axis as the user tilts their head downwardly causing anterior surface 54 of lens capsule 40 to also move downwardly. By doing so, the lower portion of the lens body which has a higher add component, moves into the optical axis and provides greater correction at near. Movement of the multifocal intraocular lens body 38 within artificial capsule bag 40 is slowed by the presence of translucent fluid 62 contained within bag 40. Translucent fluid 62 may be a liquid, gel, or sol, is preferably visco-elastic, and can be silicone or a related material or a combination of materials. However, any translucent substance capable of slowing movement of the multifocal intraocular lens body 38 within the artificial capsule bag 40 consistent with the practice of this invention is suitable.

In another embodiment of the present invention, attached to the outside edge of artificial capsule bag 40 is securer 64. Securer 64 secures artificial capsule bag 40 containing multifocal intraocular lens body 38 within the eye. Securer 64 are preferably positioned so as to extend from upper edge 58 and lower edge 60 of artificial capsule bag 40 and hold the artificial capsule bag 40 in place within either the posterior chamber, the capsular bag or remnants thereof, or anterior chamber, or a combination thereof. Haptics 64, as shown in FIGS. 2-4, are commonly used in the art. Any haptic shape, configuration, or number may be utilized in accordance with the teachings of the present invention. While haptics are satisfactory for the present invention, any other suitable securer is acceptable if a securer is desired.

Figure 5:
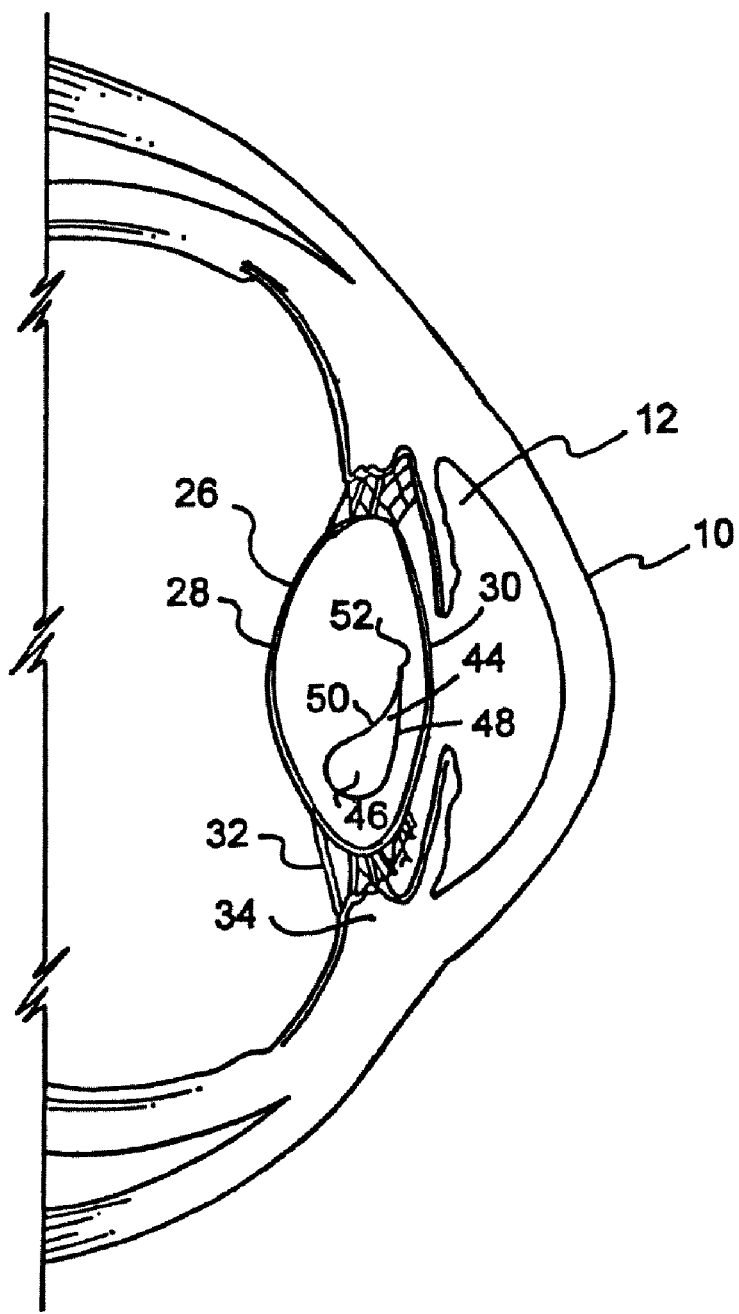
FIG. 5 is a sectional view of a human eye illustrating the present intraocular lens body inserted within the natural lens capsule of an eye.

Referring now to FIG. 5, there is illustrated multifocal intraocular lens body 38 according to another embodiment of the present invention. Multifocal intraocular lens body 38 is placed within capsular bag 26 of the human phakic eye from which the nucleus of the natural lens has been removed, i.e. the lens is enucleated. The capsular bag 26 has an anterior capsulotomy (not shown) through which the lens body 38 is inserted into the bag 26. In this embodiment the natural lens capsule 26 contains the lens body 38 rather than the artificial capsule bag 40 as described above. The anterior capsulotomy, probably small in size, may be plugged with a natural or synthetic material after the lens body is inserted and the capsular bag filled with a translucent substance. Similarly to the embodiment of the present invention that utilizes an artificial capsule bag 40, a translucent substance such as a liquid, gel, oil or sol, or any similar substance, is placed within capsular bag 26 to slow movement of the lens body 38. The structure and composition of the lens body 38 is also as described above with respect to FIGS. 2-4.

Whereas it is intended that the description of the present invention is but one embodiment for implementing the invention. Variations in the description likely to be conceived by those skilled in the art still fall within the breadth and scope of the disclosure of the present invention. It is also understood that additional applications of the present invention will be apparent to those skilled in the art upon a reading of the description and a consideration of the appended claims and drawings.

I claim:

1. A multifocal intraocular lens system for insertion of a multifocal intraocular lens into a lens capsule of an eye, said lens system comprising:
   a multifocal intraocular lens comprising a solid lens body having a substantially elliptical anterior surface on the exterior of the lens body with an upper portion and a lower portion, a substantially elliptical posterior surface on the exterior of the lens body with an upper portion and a lower portion, wherein the anterior surface is convex, the upper portion of the posterior surface is concave, and the lower portion of the posterior surface is convex, with an optical axis passing through the anterior surface and the posterior surface; wherein the lower portion of the anterior surface and the lower portion of the posterior surface meet at a bottom periphery, and the upper portion of the anterior surface and the upper portion of the posterior surface meet at a top periphery; said bottom edge having a semicircular or curved shape in cross-section along the optical axis, the lens body tapering upwards to create a tapering periphery at the top periphery, wherein the lower portion of the lens body is the thickest portion of the lens body; and said upper portions of said anterior surface and said posterior surface each having at least one radius of curvature; and
   a substance substantially surrounding said lens body;
   wherein an optical axis passes through the anterior surface and the posterior surface of said lens body.

2. The multifocal intraocular lens system of claim 1, wherein said lens body comprises a synthetic material.

3. The multifocal intraocular lens system of claim 2, wherein said synthetic material is selected from the group consisting of silicone, acrylic, and polymethylmethacrylate.

4. The multifocal intraocular lens system of claim 1, wherein said lens body has at least one index of refraction.

5. The multifocal intraocular lens system of claim 4, wherein said lens body has multiple indices of refraction.

6. The multifocal intraocular lens system of claim 5, wherein said lower portion of said lens body has a greater index of refraction or focusing power than said upper portion.

7. The multifocal intraocular lens system of claim 1, wherein said lens body is substantially aspheric.

8. The multifocal intraocular lens system of claim 1, wherein said lens body is formed of a material that is not colorless.

9. The multifocal intraocular lens system of claim 1, further wherein said substance is a member of the group consisting of silicone, gel, sol, liquid, oil, and acrylic.

10. The multifocal intraocular lens system of claim 1, further wherein said substance is capable of slowing movement of said lens body compared to movement of said lens body in the absence of said substance.

11. The multifocal intraocular lens system of claim 1, further wherein said substance is not colorless.

12. The multifocal intraocular lens system of claim 1, wherein said substance comprises a synthetic material.

13. The multifocal intraocular lens system of claim 1, wherein said lens body is colorless.

* * * * *